United States Patent [19]

Nielsen et al.

[11] Patent Number: 5,422,245
[45] Date of Patent: Jun. 6, 1995

[54] PLASMINOGEN ACTIVATOR INHIBITOR MONOCLONAL ANTIBODIES, HYBRIDOMAS, MONOCLONAL ANTIBODY PRODUCTION AND USE OF THE ANTIBODIES FOR ASSAY OF THE INHIBITORS

[75] Inventors: Lars S. Nielsen, Kokkedal; Peter A. Andreasen, Dragor; Keld Dano, Charlottenlund, all of Denmark

[73] Assignee: Fonden Til Fremme AF Eksperimental Cancerforskning, Copenhagen, Denmark

[21] Appl. No.: 900,364

[22] Filed: Jun. 18, 1992

Related U.S. Application Data

[63] Continuation of Ser. No. 752,990, Sep. 3, 1991, abandoned, which is a continuation of Ser. No. 35,995, Mar. 11, 1987, abandoned.

[30] Foreign Application Priority Data

Jul. 12, 1985 [DK] Denmark .............................. 3196/85

[51] Int. Cl.$^6$ .......................................... G01N 33/573
[52] U.S. Cl. ....................................... 435/7.4; 435/7.9; 435/960; 436/548
[58] Field of Search ............. 435/240.27, 70.21, 172.2, 435/215, 7.71, 7.5, 960, 7.4, 7.9; 530/391.7, 380, 387.1, 388.1, 388.25; 436/548; 424/3

[56] References Cited

U.S. PATENT DOCUMENTS 4,791,068 12/1988 Loskutoff et al. .................. 436/518

FOREIGN PATENT DOCUMENTS 0169549 1/1986 European Pat. Off. .
8600413 1/1986 WIPO .

OTHER PUBLICATIONS

Van Mourik et al., Purification of an Inhibitor of Plasminogen Activator (Antiactivator) Synthesized by Endothelial Cells. J. Biol. Chem 259:14914-14921 1984.
Sevier et al., Monoclonal Antibodies in Clinical Immunology. Clin. Chem 27:1797-1806. 1981.
Chemical Abstracts, vol. 104, 91986), abstract 66584r, Proc. Natl. Acad. Sci., USA, 1985, 82(24), 8710-14.
Chemical Abstracts; vol. 103 (1985), abstract 191901x, J. Lab. Clin. Med., 1985, 106(4), 408-15.
Chemical Abstracts, vol. 103 (1985), abstract 83888q, Thromb. Haemostasis, 1985, 55(3), 359-9.
Chemical Abstracts, vol. 101 (1984), abstract 167884g, Biochim Biophys. Acta, 1984, 801(2), 163-70.
Aastedt et al., Enzymes 91985) 102:145110.
Thorsen et al., Chem. Abstracts (1985) 102:20234.
Aastedt et al., Thromb. Haemostasis (1985) 53:122-125.
Yelton et al., Second Workshop On Function Properties Of Tumors Of T +B Lymph (1978) 81:1-7.
Coleman et al. J. Biol. Chem. 257:4260-64 1982.
Campbell Monoclonal Antibody Technology, Elsevier Press 1984 pp. 1-32 and 86-100.

Primary Examiner—Toni R. Scheiner
Assistant Examiner—Donna C. Wortman
Attorney, Agent, or Firm—Iver P. Cooper

[57] ABSTRACT

In a method of producing monoclonal antibodies against endothelial type plasminogen activator inhibitor and immunologically similar inhibitors myeloma cells are fused with antibody-producing cells obtained from mammals which have been immunized with said plasminogen activator inhibitor or with antibody-producing cells, which in vitro have been immunized with said plasminogen activator inhibitor and the hybridomas producing antibodies against the above mentioned inhibitor are selected. The antibody-producing cells are preferably spleen cells or lymph node cells, most preferably spleen cells, obtained from mice immunized with the above mentioned inhibitor. The monoclonal antibodies against endothelial type plasminogen activator inhibitor can be used for purification of plasminogen activator inhibitor, for removal of plasminogen activator inhibitor, from body fluids and other biological materials, for neutralization of the inhibitory activity of the plasminogen activator inhibitor and for detection, identification, immunostaining and quantification, e.g. by the ELISA technique, of plasminogen activator inhibitor in body fluids, normal or malignant cells and tissues, and other biological materials. Furthermore, as some of the monoclonal antibodies obtained bound complexes of urikinase type plasminogen activator with endothelial type inhibitor while others did not, the monoclonal antibodies obtained can be used for the quantification of free versus complex-bound inhibitor.

2 Claims, 5 Drawing Sheets

PLASMINOGEN ACTIVATOR INHIBITOR MONOCLONAL ANTIBODIES, HYBRIDOMAS, MONOCLONAL ANTIBODY PRODUCTION AND USE OF THE ANTIBODIES FOR ASSAY OF THE INHIBITORS

This is a continuation of application Ser. No. 07/752,990 filed Sep. 3, 1991, abandoned, which is a continuation of 07/035,995, filed Mar. 11, 1987, abandoned which is the national stage of PCT/DK86/00080, filed Jul. 11, 1986, the contents of all of which are hereby incorporated by reference.

TECHNICAL FIELD

This invention relates to monoclonal antibodies, a method of producing such antibodies, hybridoma cells capable of producing the antibodies and uses of the antibodies.

BACKGROUND ART

The fusion of mouse myeloma cells with spleen cells from immunized mice (Köhler and Milstein, Nature (1975), 256, 496–497) was the first indication that it is possible to obtain continuous cell lines which produce homogenous (so-called "monoclonal") antibodies. Since then, a large number of attempts have been made to produce various hybrid cells (so-called "hybridomas") and to employ the antibodies formed by these cells for various scientific investigations (cf. Current Topics in Microbiology and Immunology, volume 81—"Lymphocyte Hybridomas", F. Melchers et al., Springer-Verlag ( 1978 ) and references therein; C. J. Barnstable et al., Cell, (1978), 14, 9–20; P. Parham, W. F. Bodmer, Nature (1978 ), 276, 397–399; Handbook of Experimental Immunology, 3rd edition, vol. 2, D. M. Wier, editor, Blackwell, 1978, Chapter 25, Chem. Eng. News, 15–17 (1979); Kennett, R. H., McKearn J. T., and Bechtol, K. B. (1980) Monoclonal Antibodies. Hybridomas: A New Dimension in Biological Analysis ( Plenum, New York ) ). These reports describe the principal techniques for the production of monoclonal antibodies by hybridomas.

Monoclonal antibodies against human plasminogen activators (urokinase-type (u-PA) and tissue-type (t-PA)) and produced by hybridomas have been prepared and have been used for purification, identification, and immunochemical localization of the activators and their proenzymes (Kaltoft, K., Nielsen, L. S., Zeuthen, J., and Danø, K. (1982) Proc. Natl. Acad. Sci. USA, 79, 3720–3723; Nielsen, L. S., Hansen, J. G., Andreasen, P. A., Skriver, L., Danø, K., and Zeuthen, J. (1983) The EMBO Journal, 2, 115–119; Nielsen, L. S., Hansen, J. G., Skriver, L., Wilson, E. L., Kaltoft, K., Zeuthen, J., and Danø, K. (1982), Biochemistry, 21, 6410–6415; Danø, K., Dabelsteen, E., Nielsen, L. S., Kaltoft, K., Wilson, E. L., and Zeuthen, J. (1982), J. Histochem, Cytochem., 30, 1165–1170). Andreasen, P. A., Nielsen, L. S., Grøndahl-Hansen, J., Skriver, L., Zeuthen, J., Stephens, R. W., and Danø, K. (1984) The EMBO Journal, 3, 51–56). It has recently been shown that inhibitors of plasminogen activators play an important role in the regulation of the plasmin mediated proteolysis. Such inhibitors have been identified in a variety of tissues, body fluids and cultured cell lines (Holmberg, L, Lecander, I., Persson, B., and Åstedt, B. (1978), Biochim. Biopys. Acta, 544 128–137; Seifert, S. C. and Gelehrter, T. D. (1978) Proc. Natl. Acad. Sci. USA, 75, 6130–6133; Chmielewska, J., Rånby, M., and Wiman, B. (1983 ) Thromb. Res., 31, 427–431; Emeis, J. J., Van Hindsbergh, V. W. M., Verheijen, J. H. and Wijngaards, G. (1983) Biochem. Biophys. Res. Commun., 110, 391–398; Golder, J. P. and Stephens, R. W. (1983) Eur. J. Biochem., 136, 517–522; Loskutoff, D. J., van Mourik, J. A., Erickson, L. A., and Lawrence, D. (1983), Proc. Natl. Acad. Sci. USA, 80, 2956–2960; Philips, M., Juul, A. -G., and Thorsen, S. (1984) Biochim. Biophys. Acta, 802, 99–110; Vassalli, J. -D., Dayer, J. -M., Wohlwend, A. and Belin, D. (1984)J. Exp. Med., 159, 1653–1668; Erickson, L. A., Ginsberg, M. H., and Loskutoff, D. J. (1984), J. Clin. Invest., 74, 1465–1472; Cwikel, B. J., Barouski-Miller, P. A., Coleman, P. L., and Gelehrter, T. D. (1984), J. Biol. Chem., 259, 6847–6851; Åstedt, B., Lecanders, I., Brodin, T., Lundblad, A., and Löw, K. (1985), Thrombos. Haemost., 53, 122–125; J. Biol. Chem. (1985), 260, 7029–7034). The mutual relationship of these inhibitors is at present not fully clarified, although recent evidence indicates that at least three immunologically dissimilar types of plasminogen activitor inhibitors exist. These include (1) protease nexin, (2) plasminogen activator inhibitor purified from placenta (Åstedt, B., Lecander, I., Brodin, T., Lundblad, A., and Löw, K., (1985) Thromb. Haemost. 53, 122–125), and (3) plasminogen activator inhibitors that inhibit u-PA and t-PA and which typically have been obtained from human endothelial cells, human blood platelets, and rat hepatoma cells (HTC), in the following referred to as endothelial type plasminogen activator inhibitor (e-PAI).

An inhibitor with remarkable similarities to e-PAI has been found in human plasma (Thorsen, S. and Philips, M. (1984) Biochim. Biophys. Acta 802, 111–118).

Monoclonal antibodies against placental plasminogen activator inhibitor have been prepared and such antibodies have been used for the purification of said inhibitor (Åstedt, B., Lecander, I., Brodin, T., Lundblad, A., and Löw, K., (1985) Thrombs. Haemost. 53, 122–125).

DISCLOSURE OF INVENTION

The present invention provides monoclonal antibodies against the endothelial type plasminogen activator inhibitor and immunologically similar inhibitors.

The term "immunologically similar inhibitors" denotes plasminogen activator inhibitors which cross-react with polyclonal or monoclonal antibodies raised against inhibitors derived from any of the sources mentioned in connection with the above definition of endothelial type plasminogen activator inhibitor.

The provision of these antibodies makes it possible to study the role of plasminogen activator inhibitors in plasmin mediated proteolysis including fibrinolysis and the mutual relationship of the above mentioned plasminogen activator inhibitors. Moreover, such monoclonal antibodies are useful for the purification of plasminogen activator inhibitor by means of immunoadsorption chromatography, for removal of the inhibitor from body fluids and other biological materials by means of immunoadsorption, for neutralization of the inhibitory activity of the plasminogen activator inhibitor and for the detection, identification and quantification, e.g. by the ELISA technique, of plasminogen activator inhibitor in body fluids, normal or malignant cells and tissues, and other biological materials.

The invention also provides a method of producing the above mentioned antibodies. This method comprises fusing myeloma cells with antibody-producing cells obtained from mammals which have been immunized with endothelial type plasminogen activator inhibitor or immunologically similar inhibitors or with antibody-producing cells which in vitro has been immunized with said plasminogen activator inhibitor, and selecting the hybridomas producing antibodies against the above mentioned inhibitors. Thus the hybridomas are produced by a derivation of the method of Köhler and Milstein mentioned above. The antibody-producing cells used are preferably spleen cells or lymph node cells. The particular species of mammals from which the myeloma and antibody producing cells are derived is not critical insofar as it is possible to fuse the cells of the one species with another, e.g. mouse to rat, rat to human, or mouse to human.

It is preferred, however, to use the same species of animal as a source of both myeloma and anti plasminogen activator inhibitor antibody-producing cells. One preferred cell line for the practice of this invention is a fused cell hybrid between a plasminogen activator inhibitor primed mouse spleen cell and a mouse myeloma cell.

The hybridomas resulting from the fusion are systematically examined for production of antibodies which selectively react with plasminogen activator inhibitor.

It should be noted that monoclonal antibodies raised against a single antigen may be distinct from each other depending on the determinant that induced their formation; but for any given hybridoma (clone), all of the antibodies it produces are monospecific for a particular antigenic determinant in the plasminogen activator inhibitor molecule.

The invention also relates to hybridoma cells capable of producing monoclonal antibodies against the endothelial type plasminogen activator inhibitor and immunologically similar inhibitors.

In general, the production of the hybridomas comprises the following steps:

A. Immunization of mammals with partially purified plasminogen activator inhibitor. Balb/c-mice have been found useful for this purpose, but other mammals can also be used. The immunization scheme and the concentration of plasminogen activator inhibitor should be selected such that adequate amounts of antigen-stimulated lymphocytes are formed.

B. Obtaining the spleens or lymph nodes of the immunized mammals and preparation of a spleen cell suspension-or a lymph node cell suspension in a suitable medium.

C. Fusion of the suspended spleen cells or lymph node cells with myeloma cells of a suitable cell line (for example NS1-Ag 4/1 myeloma cells), using a suitable fusion promotor (for example polyethlene glycol). A ratio of about 10 spleen cells or lymph cells per myeloma cell is preferred. A total volume of about 1 ml of fusion medium is adequate for $10^8$ spleen cells or lymph node cells. The myeloma cell line used should preferably be of the so-called "drug resistant" type, so that, in a selective medium, unfused myeloma cells die whilst hybrids survive. Cell lines resistant to 8-azaguanine, which cells lack the enzyme hypoxanthine-guanine phosphoribosyltransferase and which therefore cannot grow in a HAT medium (hypoxanthine, aminopterin, thymidine), are most frequently used.

The myeloma cell line used should also preferably be of the "non-secreting" type so that it does not itself form antibodies or H or L chains of immunoglobulins.

D. Dilution and cultivation in individual vessels of the unfused spleen cells or lymph node cells, the unfused myeloma cells and the fused cells in a selective medium, in which the unfused myeloma cells do not divide so that the unfused cells die (about 1–2 weeks). The individual fused cells are isolated by adjusting the volume of the diluent so that a given number of cells (about 1–4) is placed in each individual vessel (for example each well of a microtitre plate). The medium (for example HAT medium) prevents the growth of the resistant (for example against 8-azaguanine) unfused myeloma cell line, and thus it dies. The unfused spleen cells or lymph node cells have only a limited number of division cycles and hence these cells also die after a certain period (about 1–2weeks). In contrast, the fused cells continue to divide since they have inherited permanent growth from the parent myeloma cells and the ability to synthesize the enzyme hypoxanthine-guanine phosphoribosyltransferase from the parent spleen cells or lymph node cells, and thus they are able to survive in the selective medium.

E. Checking for the presence of antibodies against plasminogen activator inhibitor in each vessel.

F. Selecting (for example by limiting dilution) and cloning the hybridomas which produce the desired antibody.

When the desired hybridoma has been selected and cloned monoclonal antibodies of very high purity are obtained when the hybridomas are cultured in a suitable medium for a certain time and the antibody is obtained and purified from the supernatent. A suitable medium and the optimum culture time can easily be determined. This in vitro technique provides monoclonal antibodies which are contaminated with only small amounts of proteins from the heterologous serum (for example fetal calf serum).

In order to produce a significantly higher concentration of monoclonal antibodies of only very slightly reduced purity, the selected hybridoma can be injected into a, preferably syngeneic or semisyngeneic, mouse. After a certain incubation time, this leads to the formation of a tumour in the mouse which releases high concentrations of antibody (5–20 mg/ml) in the blood and in the peritoneal exudate (ascites) of the host animal. Even though these mice have normal antibodies in the blood and ascites, nevertheless these only arise at a concentration of about 5% of the monoclonal antibodies.

BRIEF DESCRIPTION OF DRAWINGS

The invention will now be described in more detail with reference to the drawings in which.

MODES FOR CARRYING OUT THE INVENTION

The invention will be described in further detail with reference to the examples. Examples 1 to 5 illustrate the production and use of monoclonal antibodies against an endothelial type plasminogen activator inhibitor (e-PAI) released-into the culture fluid from dexamethasone-treated human fibrosarcoma cells. The inhibitor inhibits human urokinase-type plasminogen activator (u-PA) and tissue-type plasminogen activator (t-PA).

EXAMPLE 1

Production of the antigen used for immunization

Inhibitor was purified from serum-free conditioned culture fluid of dexamethasone-treated human fibrosarcoma cells of the line HT1080 (ATCC CCL121) by a procedure adapted from that described by van Mourik, J. A., Lawrence, D. A., and Loskutoff, D. J. (1984) J. Biol. Chem. 259, 14914–14921 for the plasminogen activator inhibitor from bovine endothelial cells. The HT-1080 cell line was maintained as a monolayer culture, using Dulbecco-modified Eagle's medium supplemented with 10% fetal bovine serum. Serum-free culture fluid was prepared from confluent monolayer cultures. Dexamethasone, a synthetic glucocorticoid, was added to the serum-free cultures in a concentration of $10^{-6}$M. HT-1080 cells produce relatively high amounts of u-PA, which under the culture conditions used is in the proenzyme form. Before purification of inhibitor, the culture fluid was depleted of u-PA by passing it through a column of monoclonal anti-u-PA IgG immobilized on Sepharose (Nielsen, L. S., Hansen, J. G., Skriver, L., Wilson, E. L.,. Kaltoft, K., Zeuthen, J., and Danø K. (1982) Biochemistry, 24, 6410–6415). The culture fluid was then applied to a column of concanavalin A-Sepharose equilibrated with 0.01 M sodium phosphate, pH 7.4, 0.15 M NaCl (PBS), at a flow rate of 30 ml per h, using 5 ml Concanavalin A-Sepharose per liter culture fluid. The column was washed with 5 column volumes of PBS with 0.3M NaCl. Bound protein was eluted with PBS with 0.5M NaCl and 0.2M α-methyl-D-mannoside. Fractions containing the peak of protein, as determined by measuring the absorbancy at 280 nm, were pooled and used for further analysis.

From photometric scanning at 600 nm of Coomassie Blue stained polyacrylamide gels, the partly purified preparation was estimated to contain approximately 75% of a $M_r \sim 54,000$ protein, the electrophoretic mobility of which coincided with inhibitory activity as determined by reverse zymography (see below). Before immunization this preparation was dialysed against PBS.

Immunization of BALB/c-mice

4 BALB/c-mice were immunized intradermally with approximately 20 μg of the $M_r \sim 54,000$ protein obtained above in Freund's incomplete adjuvant on day 0, 7, 14, and 21. The plasma of each mouse was analyzed by ELISA (Enzyme Linked immunosorbent Assay) and the mouse showing the highest titer against the immunization preparation was chosen for intraveneous injection and fusion with myeloma cells. The intraveneous injection of a similar dose as above dissolved in PBS was given on day 28 and the spleen was removed 3 days later.

Cell fusion and culture of cells

Spleen cells were mixed with NSl-Ag 4/1 myeloma cells (resistant to 0.1 mM 6-thioguanine; synthesize but do not secrete kappa light chains) (Köhler and Milstein (1976) Eur. J. Immunol. 6, 511–519) in a ratio of 10:1 ($10^8$ spleen cells to $10^7$ NSl-Ag 4/1 cells) and incubated with 1 ml of 50% (wt/vol) polyethylene glycol in a phosphate-buffered saline solution for 90 sec. at 37° C. Dulbecco's modified Eagle's medium (20 ml) was added to the suspension, and the cells were centrifuged at 1000 ×g. The cell pellet was resuspended in 96 ml of hypoxanthine/aminopterin/thymidine medium (Littlefield, J. W. (1964) Science 145, 709–710) supplemented with 10% fetal bovine serum and was distributed in 48 wells of Costar trays (Costar, Cambridge, M. A.). The medium was changed twice weekly.

Selection of hybridomas

For screening of hybridoma supernatants using ELISA (Enzyme Linked Immunosorbent Assay), wells of Immuno Plates were coated with 100 μl per well of concanavalin A-Sepharose-purified plasminogen activator inhibitor containing ~4 μg of protein per ml in 0.1M $Na_2CO_3$, pH 9.8 over night at 37° C. In order to block residual binding sites, the wells were incubated with 0.25% BSA in PBS for more than 15 minutes. Then the wells were incubated with hybridoma supernatants for 1 hour and finally with peroxidase-conjugated rabbit antibodies against mouse Ig (Dakopatts, Copenhagen, Denmark) diluted 1:800 in PBS with 0.1% Tween 20 for 1 hour. Peroxidase reaction was performed for 5 min. with 100 μl of 0.1% o-phenylenediamine 0.01% $H_2O_2$ in 0.1M citrate-phosphate pH 5.0. The reaction was stopped by the addition of 100 μl 1M $H_2SO_4$, and absorbahoy was read at 492 nm.

For screening by immunoblotting, proteins in 10 ml serum-free medium from HT-1080 cells were concentrated by precipitation with trichloroacetic acid and separated by SDS-PAGE in a 10 cm wide lane. The proteins were transferred electrophoretically (10 V, 250 mA for 16 h at room temperature) from the polyacrylamide gel to nitrocellulose paper. The transfer buffer used was 0.125M Tris HCl, 0.19M glycine 20% (v/v) methanol 0.1% (w/v) SDS, pH 8.6. The nitrocellulose paper was washed in 0.05M Tris HCl, pH 7.4, 0.15M NaCl 1% Triton X-100 (TBS-Triton) for 15 min. at room temperature and incubated for 30 min. with TBS-Triton containing human serum albumin (10 mg/ml). The paper was then washed 2×15 min. in TBS-Triton. Vertical lanes were cut out and incubated overnight at 4° C. with culture supernatants from the hybridomas. The lanes were washed in TBS-Triton 3×15 min., incubated for 1 h at room temperature with peroxidase-conjugated rabbit IgG anti-mouse immunoglobulins (diluted 1:50 in TBS-Triton), and washed 3×10 min. in 0.05M Tris-HCl, pH 7.6. The peroxidase reaction was then performed with 0.5 mg/ml of di-aminobenzidine in 0.01% $H_2O_2$ for 5 min. at room temperature.

As a control nitrocellulose lanes were incubated with supernatant from hybridomas (Hy 2.15) producing antibody of irrelevant specificity (anti-trinitrophenyl) (Shulman, M., Wilde, C. D., and Köhler, G. (1978) Nature, 276, 269).

After 10 days cultivation of the hybriclomas supernatant from 16 primary wells showed a strongly positive ELISA-reaction. The hybridomas from said wells were cloned and recloned by limiting dilution (Kennett, R.

H., McKearn, J. T., and Bechtol, K. B. (1980) Monoclonal Antibodies. Hybridomas: A New Dimension in Biological Analysis (Plenum, New York)). After cloning and recloning 4 stable ELISA-positive clones remained. Immunoblotting analysis showed that all four clones produced antibody which reacted with an $M_r \sim 54,000$ band in crude conditioned culture fluid from HT-1080 cells.

Purification of antibodies

Monoclonal antibodies produced by the 4 clones obtained were purified from hybridoma culture fluid on a protein A-Sepharose column as follows: 200 ml of conditioned culture fluid from hybridomas was applied to a 5 ml protein A-Sepharose column (12×43 ram). The column was washed with 30 ml 0.1M Tris HCl, pH 8.1. Elution was performed with 0.1M sodium acetate, pH 4.0, 0.15M NaCl. Fractions of 2 ml were collected in tubes containing 200 μl 1M Tris-HCl, pH 9.0. The IgG concentration in the purified preparation was determined by spectrophotometry at 280 nm ($A_{280}^{1\%}{}_{nm}=14$). Concentrations of IgG in impure solutions were determined by single radial immunodiffusion using purified mouse IgG as a standard.

Characterisation of the antibodies produced by the cloned hybridomas

The classes and subclasses of the antibodies produced by the hybrid clones were analysed by immunodiffusion against class-and subclass-specific goat antibodies (Meloy, V. A., USA). All 4 antibodies produced by the 4 clones were of the $IgG_1$ subclass.

Isoelectric focusing of the 4 purified monoclonal antibodies in slab gels containing 6% polyacrylamide and 6% carrier ampholyte solution (Pharmalyte) showed that their isoelectric points were different (ranging between 5 and 7.5). The binding characteristics of the antibodies to solid-phase inhibitor as measured by ELISA differed greatly. They were therefore considered to originate from different hybridization events. The four clones were designated anti-plasminogen activator inhibitor clone 1, 2, 3, and 4, respectively.

Figure 1:
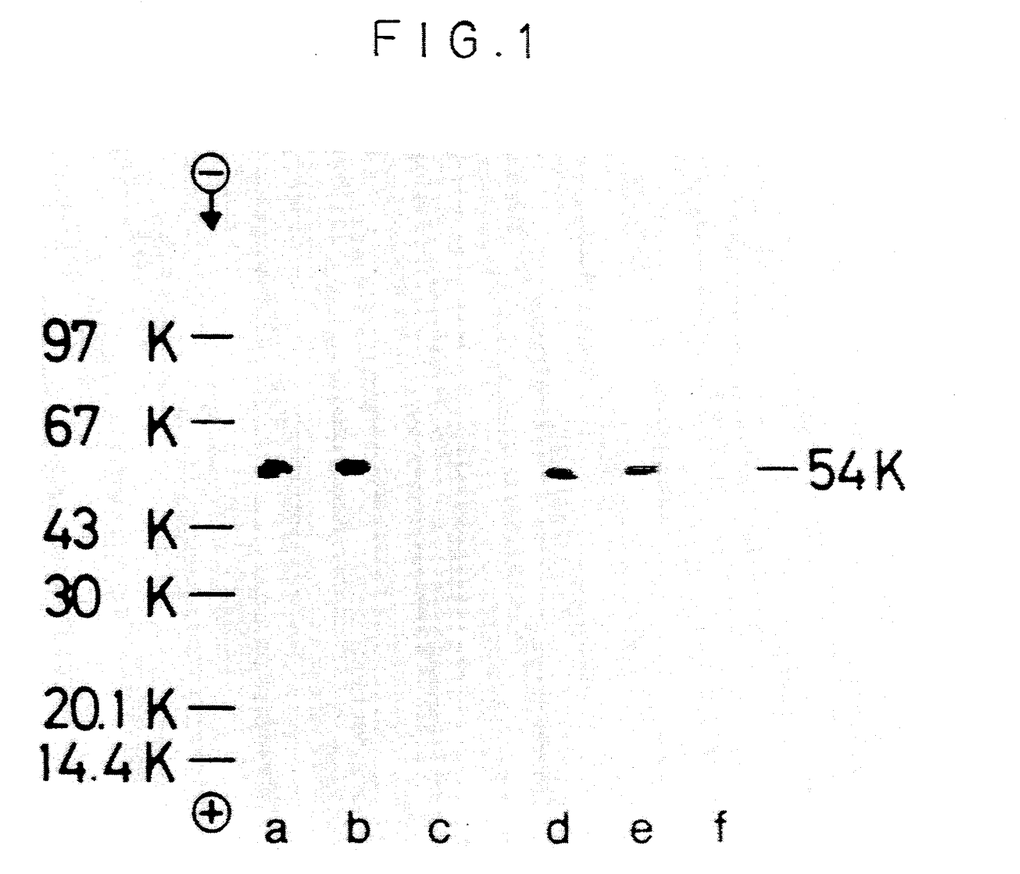
FIG. 1 is a zymogram showing reverse zymography for plasminogen activator inhibitor in culture fluid conditioned by dexamethasone-treated human fibrosarcoma cells of the line HT-1080 or umbilical cord endothelial cells before and after passage through Sepharose columns coupled with monoclonal antibodies against trinitrophenyl (control) and e-PAI.

Cross-reaction of antibodies against plasminogen activator inhibitor from human fibrosarcoma cells with other plasminogen activator inhibitors, Conditioned culture fluid from human umbilical cord endothelial cells also contains a plasminogen activator inhibitor detectable by reverse fibrin-agarose zymography (Sprengers, E. O., Verheijen, J. H., van Hindsberg, V. W. M., and Emeis, J. J. (1984) Biochim. Biophys. Acta. 801, 163–170). This inhibitor has an electrophoretic mobility indistinguishable from that of the HT-1080-inhibitor. FIG. 1 is a zymogram showing reverse zymography for plasminogen activator inhibitor in culture fluid conditioned by HT-1080 cells (a–c) or umbilical cord endothelial cells (d–f) before (a, d) and after passage of Sepharose columns coupled with monoclonal antibodies against TNP (b, e) and against HT-1080 plasminogen activator inhibitor (c, e). For coupling procedure see example 2. Two one ml columns containing approximately 1 mg of monoclonal anti-TNP IgG and monoclonal anti-plasminogen activator inhibitor IgG from clone 1, respectively, were equilibrated with a buffer containing 0.1M Tris HCl, pH 8.1, 0.1% Triton X-100. To both columns was added 1 ml of serum-free cell culture fluid from HT-1080 cells and the run-through was collected. Serum-free cell culture fluid from human umbilical cord endothelial cells was treated identically. After electrophoresis, the gel was processed for reverse zymography for plasminogen activator inhibitors with an incubation period of 1.5 hours. Reverse zymography was carried out as described by Eriksson, L. A., Lawrence, D. A., and Loskutoff, D. J. (1984) Anal. Biochem. 137, 454–463. Plasminogen activator inhibitors in SDS polyacrylamide gels are detected by layering the gels over agarose gels containing fibrin, plasminogen, and plasminogen activator. Inhibitors diffuse into the fibrin/plasminogen/plasminogen activator gel from the polyacrylamide gel, and their presence is revealed by zones of fibrin resistant to plasminogen activator-catalyzed lysis. The position of $M_r$-markers are indicated.

Passage of HT-1080 medium through the Sepharose column with antibodies from anti-inhibitor IgG clone 1 removed the inhibitory activity as revealed by reverse fibrin-agarose zymography; there was no effect of passage through a control column with a monoclonal control antibody (anti-TNP IgG). When plasminogen activator inhibitor from said human endothelial cells are applied to the column with monoclonal antibodies from clone 1 the inhibitor is bound to the column (FIG. 1). When columns with the antibodies from clone 2, 3, or 4 were used, the results were identical (results not shown). This demonstrates immunological similarities between this inhibitor and the HT-1080 plasminogen activator inhibitor.

Using the same technique we have also shown that rabbit antibodies against the HT-1080-inhibitor crossreact with a plasminogen activator inhibitor extracted from human blood platelets prepared by the method described by Erikson, L. A., Ginsberg, M. H., and Loskutoff, D. J. (1984), J. Clin. Invest., 74, 1465–1472.

It has been reported that the endothelial cell plasminogen activator inhibitor, the platelet inhibitor (Erikson, L. A., Ginsberg, M. H., and Loskutoff, D. J. (1984), J. Clin. Invest., 74, 1465–1472) and the inhibitor from rat hepatoma cells of the HTC line show immunological similarities (D. J. Loskutoff and T. D. Gelehrter, personal communication). Thus it appears that the HT-1080-inhibitor is similar to a number of plasminogen activator inhibitors isolated from different cells and tissues.

EXAMPLE 2

Immunosorbent purification of inhibitor

After coupling to Sepharose, antibody produced by anti-plasminogen activator inhibitor clone 1 was used for purification of inhibitor from HT-1080 cell culture fluid by a column procedure. 8 mg of monoclonal antibodies from anti-inhibitor IgG clone 1 was coupled to 2 ml of cyanogen bromide-activated Sepharose 4B. The material was packed in a column (20×16 mm), which was equilibrated with 0.1M Tris HCl, pH 8.1. Conditioned cell culture fluid from HT-1080 cells was applied at a flow rate of 50 mi/hr. The column was washed with equilibration buffer (flow rate 50 ml/hr) followed by 0.1M Tris HCl. pH 8.1, 1M NaCl (flow rate 50 ml/hr). Elution was performed at a flow rate of 25 ml/h with 0.1M $CH_3COOH$, DH 2.7, collecting fractions of 2 ml into tubes containing 200 μl of 1M Tris HCl, pH 9,0 in order to neutralize the eluate. Fractions containing protein as determined by absorbance measurements at 280 nm were pooled.

For quantification of inhibitory activity 0.005 Ploug Units urokinase standard in 25 μl of assay buffer was mixed with 25 μl of inhibitor diluted in the same buffer; this mixture was diluted to 500 μl with assay buffer and added to [$^{125}$I]-fibrin plate wells (see example 3). From assays with fixed concentrations of urokinase standard and serial dilutions of inhibitor preparations, the dilution of inhibitor causing 50% inhibition of the urokinase standard was calculated. The amount of inhibitor in wells with 50% inhibition was defined as 0.0025 inhibitor unit (Inh. U.). Before assay, inhibitor preparations were treated with SDS to a final concentration of 0.1%, and after a one hour incubation at 25° C. Triton X-100 was added to a final concentration of 1%.

Results from the purification of inhibitor from human fibrosarcoma cells are shown in table I.

TABLE 1

Purification of inhibitor from human fibrosarcoma cells by monoclonal antibody coupled to Sepharose

| Fraction | Volume ml | Protein mg | Total inhibitory activity Inh. Units | Specific inhibitory activity Inh. Units/mg | Yield % |
| --- | --- | --- | --- | --- | --- |
| Conditioned culture fluid applied to column | 740 | 59.9 | 19,200 | 321 | 100 |
| Run through | 740 | ND | 2,600 | ND | 14 |
| Wash 1 | 10 | ND | ND | ND | ND |
| Wash 2 | 40 | ND | ND | ND | ND |
| Eluate | 14.2 | 1.14 | 16,400 | 14,400 | 85 |

Figure 2:
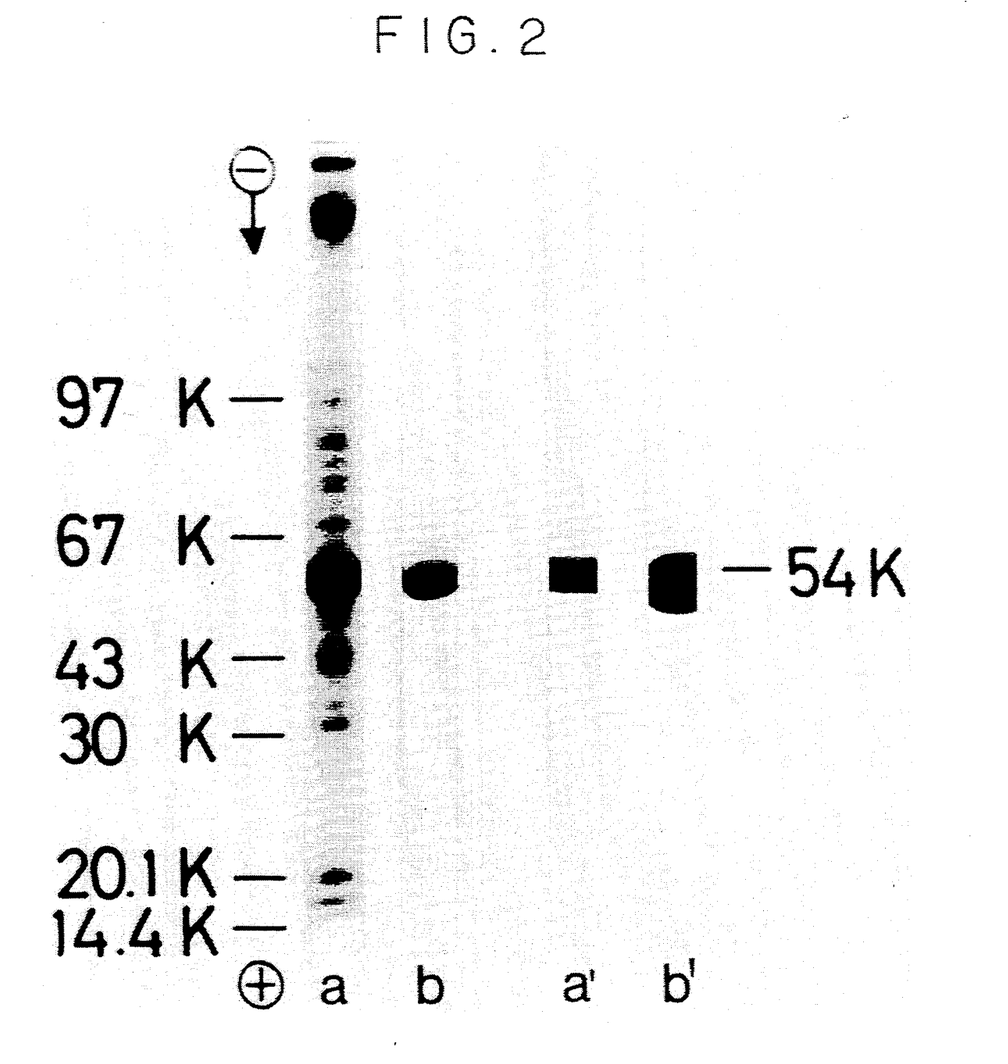
FIG. 2 is a photography showing SDS-PAGE and reverse fibrin agarose zymography of HT-1080 cell medium and e-PAI purified by immunosorbent chromatography with a monoclonal antibody against e-PAI.

As shown in table I 86% of the inhibitory activity was bound by the column. After washing 99% of the inhibitory activity bound to the column could be eluted at low pH. A 45-fold purification of inhibitory activity was obtained and the eluate contained only an $M_r \sim 54,000$ protein band as evaluated by Coomassie Blue staining of a SDS-polyacrylamide gel. The electrophoretic mobility of this protein coincided with the mobility of inhibitory activity as determined by reverse fibrin-agarose zymography (FIG. 2). The samples subjected SDS-polyacrylamide gel electrophoresis (SDS-PAGE) were: 1.5 ml crude culture fluid from HT-1080 cells (a), eluate corresponding to 10 µg of protein (b), 10 µl crude culture fluid from HT-1080 cells (a'), and eluate corresponding to 50 ng protein (b'). After electrophoresis, the gels were either stained with Coomassie Blue (a, b), or inhibitor in the gels was visualized by reverse fibrin agarose zymography for 2 hours (a', b'). The position of the following markers are indicated: Rabbit phosphorylase b (97K), Bovine serum albumin (67K), ovalbumin (43K), carbonic anhydrase (30K), soybean trypsin inhibitor (20.1K), and α-lactalbumin (14.4K).

As judged from spectrophotometric scannings of stained polyacrylamide gels with crude culture fluid and the purified preparation, the strong $M_r \sim 54,000$ band was purified to the same extent as the inhibitory activity. SDS-PAGE in slab gels with a 6–16% linear concentration gradient of polyacrylamide of crude culture fluid and run-through from the immunosorbent column showed that the $M_r \sim 54,000$ band was greatly diminished, while no other bands were affected (results not shown).

SDS-PAGE under reducing conditions showed one band with $M_r \sim 54,000$, indicating that the purified inhibitor consisted of one polypeptide chain (results not shown).

EXAMPLE 3

Neutralization of inhibitory activity

Figure 3:
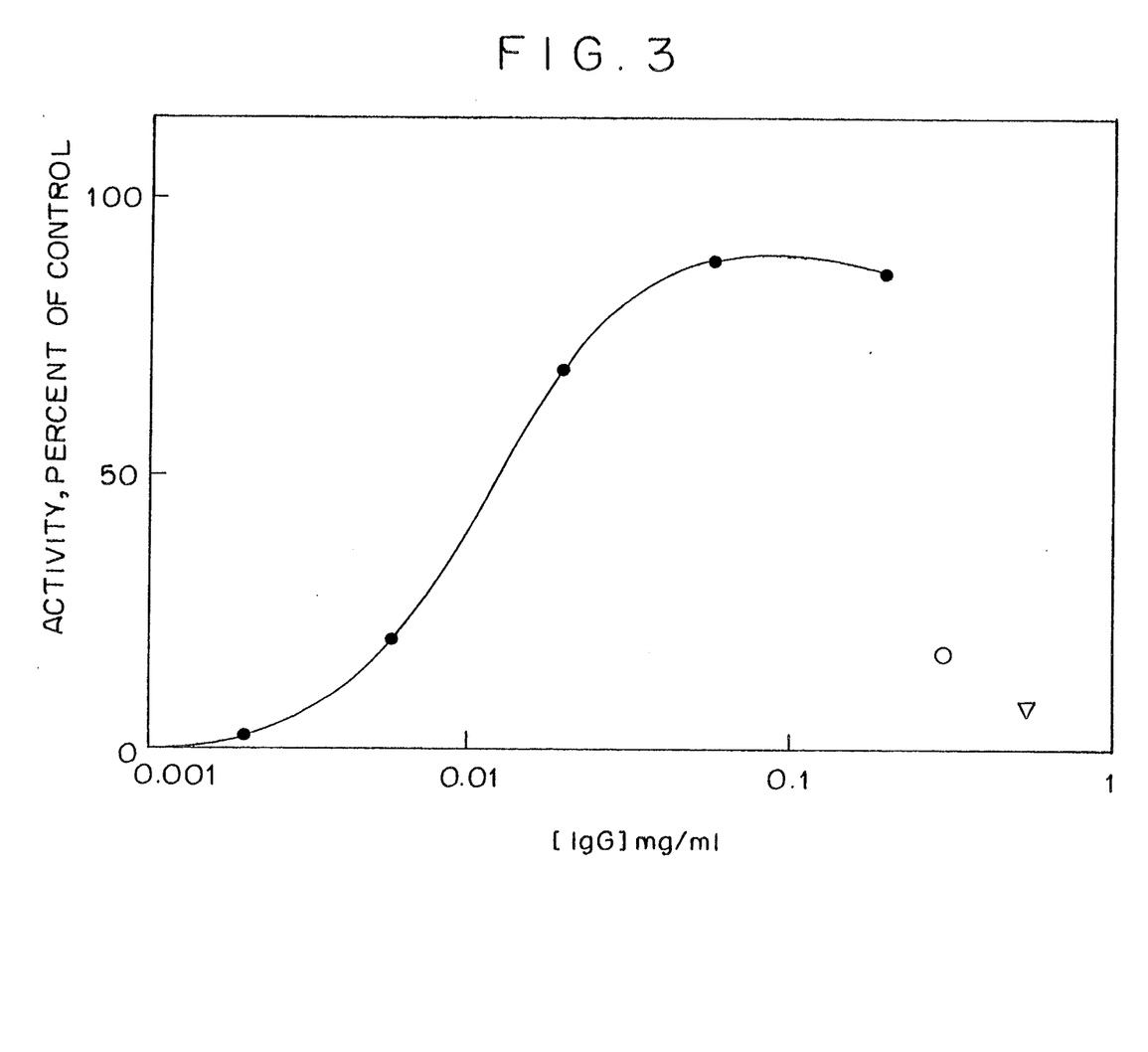
FIG. 3 is a graph showing neutralization of inhibitory action of e-PAI by monoclonal antibody against e-PAI.

The effect of the monoclonal antibodies on the inhibitory activity of the inhibitor was tested by a [$^{125}$I]-fibrin plate assay, which involved the activation of plasminogen by u-PA and the subsequent degradation of [$^{125}$I]-fibrin by the plasmin formed (cf. Nielsen, L. S., Hansen, J. G., Andreasen, P. A., Skriver, L., Dan , K., and Zeuthen, J. (1983) EMBO J., 2, 115–119). The [$^{125}$I]-fibrin plate assay was carried out as follows: 10 ng of inhibitor was added to [$^{125}$I]-fibrin plate assay wells together with 0.2 ng active u-PA, 1 µg Glu-plasminogen and IgG as indicated, in a total volume of 500 µl 0.1M Tris HCl, pH 8.1, 0.1% Triton X-100, 0.25% gelatine (assay buffer). Radioactivity released in parallel control assays without u-PA (approximately 500 cpm) was subtracted and the radioactivity released in the presence of inhibitor calculated as a percentage of that released in the absence of inhibitor (approximately 3000 cpm). The total radioactivity in the [$^{125}$I]-fibrin plate assay wells was approximately 60,000 cpm. Each point represents the mean of two determinations. A neutralization of inhibitory activity that increased with increasing concentrations of anti-inhibitor IgG from clone 2 was observed (FIG. 3, (●)) while there was no significant effect on inhibition of antibodies from clone 1 (FIG. 3 (o)) and the monoclonal control antibody of irrelevant specificity (anti-TNP IgG) (FIG. 3 (∇)). No neutralizing effect was observed with anti-inhibitor IgG from clone 3 and 4 (results not shown).

EXAMPLE 4

Binding of uPA/inhibitor complexes to monoclonal anti-inhibitor antibodies.

Figure 4:
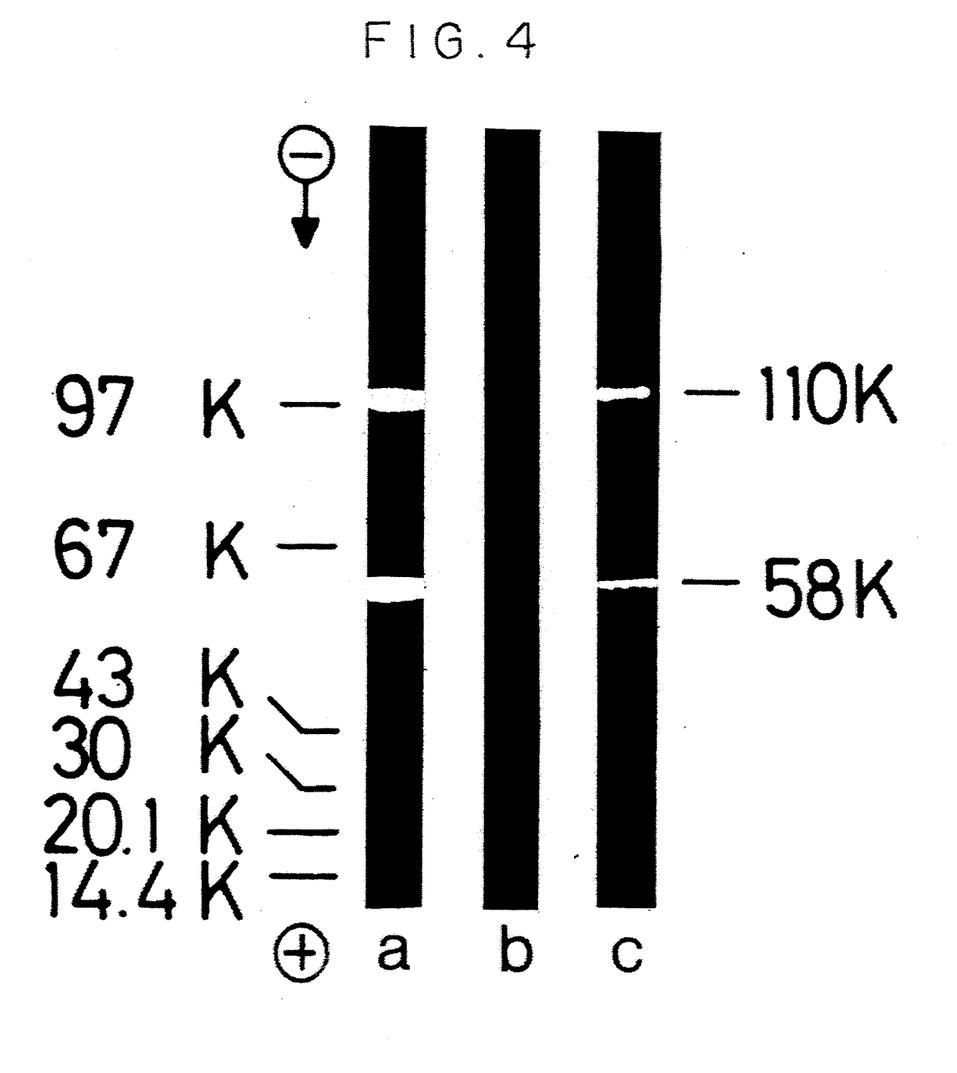
FIG. 4 is a zymogram showing binding of complexes of u-PA with e-PAI to Sepharose columns with monoclonal antibodies against e-PAI.

It has been shown that u-PA forms an equimolar complex with the HT-1080 inhibitor. This complex has an electrophoretic mobility corresponding to $M_r \sim 110,000$ in SDS-PAGE and is detectable because it regains its plasminogen activator activity as measured by fibrin-agarose zymography: Plasminogen activator activity in polyacrylamide gels is detected by layering the gels over agarose gels containing fibrin and plasminogen—the plasminogen activators diffuse into the agarose gels and activate plasminogen to produce visible lysis zones (Granelli-Piperno, A. and Reich, E. (1978) J. Exp. Med., 148, 223–234). FIG. 4 is a zymogram showing the binding of complexes of u-PA and HT-1080-inhibitor to Sepharose columns with monoclonal antibodies against the HT-1080 inhibitor. One ml columns containing approximately 1 mg of monoclonal anti-TNP antibody (c) antibodies from anti-inhibitor IgG clone 1 (a), or monoclonal anti-plasminogen activator inhibitor IgG from clone 2 (b) were equilibrated with a buffer containing 0.1M Tris HCl, pH 8.1, 0.1% Triton X-100, 0.25% gelatin. One ml u-PA-inhibitor complex obtained by incubating the activator (25 ng/ml) with the inhibitor (500 ng/ml) for 1 h at 25° C. in a buffer of 0.1M Tris-HCl, pH 8.1, 0.1% Triton X-100 was added to each column, and 75 μl of the run-through from each column was subjected to SDS-PAGE followed by zymography for plasminogen activators. The positions of $M_r$-markers are indicated. Antibodies from anti-inhibitor clone 2 bound these complexes, while no binding was observed with antibodies from anti-inhibitor clone 1 or anti-TNP. Likewise, monoclonal anti-plasminogen activator inhibitor IgG from clone 4 bound complexes, while antibodies from 3 did not (results not shown). Said differential reactivities can be used in the quantitation of free versus complex-bound inhibitor.

EXAMPLE 5

Immunocytochemical localization of the inhibitor

The monoclonal anti-plasminogen activator inhibitor antibodies can be used for immunocytochemical localization of the inhibitor in normal or malignant cells and tissues.

Figure 5:
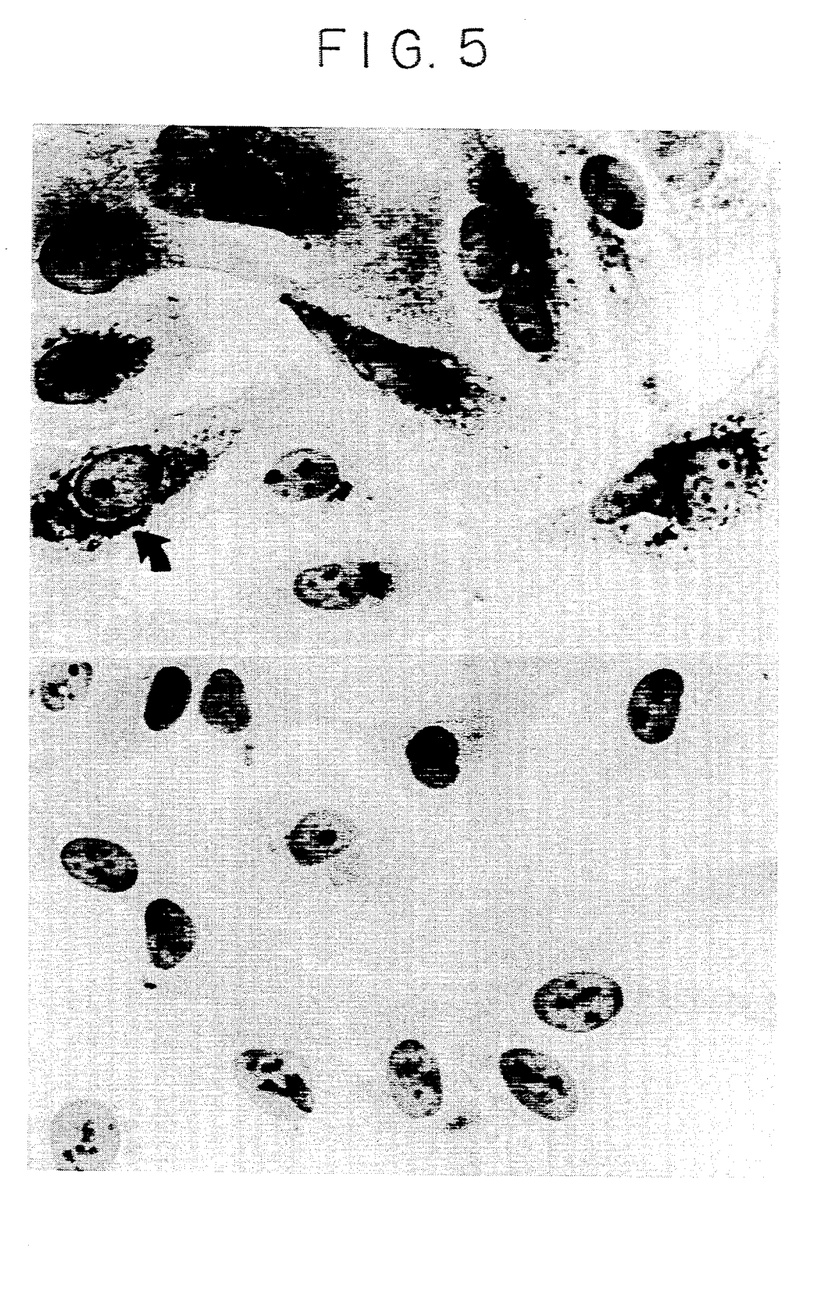
FIG. 5 is a photography showing immunoperoxidase staining of HT-1080 cells with a monoclonal antibody against e-PAI.

HT-1080 cells cultured in serum free medium in the presence of dexamethasone were seeded on microscope slides and fixed for 30 min. with 4% paraformaldehyde in 0.1M sodium phosphate buffer, pH 7.3. After washing with 0.05M Tris-HCl, pH 7.4, 0.15M NaCl (TBS) containing 1% Triton X-100 (TBS-Triton) for 30 min the cells were exposed to 10% rabbit serum in TBS for 30 min. and incubated overnight at 4° C. with purified monoclonal antibody (10 μg/ml) diluted in TBS with 10% rabbit serum. Following a 1 h temperature reequilibration, the cells were washed with TBS-Triton and bound monoclonal antibody was demonstrated by incubation with peroxidase conjugated rabbit anti-mouse IgG (1:60) diluted in TBS with 10% rabbit-serum followed by development with diaminobenzidine-hydrogen peroxide. The cells were lightly counterstained with haematoxylin, dehydrated, mounted and photographed. A strong granular staining was observed often with a perinuclear localization together with a weak diffuse staining apparently distributed in the entire cytoplasm (FIG. 5, top). A distinct granular staining was observed using antibody from all 4 clones (results shown for clone 1 only). When the monoclonal anti-inhibitor antibody was substituted by monoclonal IgG of irrelevant specificity (anti-TNP antibody) (FIG. 5, bottom) or by buffer alone, no staining was seen.

The invention has been illustrated with reference to the production and use of monoclonal antibodies against a $M_r \sim 54,000$ plasminogen activator inhibitor released into the culture fluid from dexamethasone-treated human fibrosarcoma cells, but since said inhibitor is immunologically similar to the plasminogen activator inhibitors derived from human endothelial cells, human platelets and rat hepatoma cells, it should be understood that monoclonal antibodies against plasminogen activator inhibitors from these sources and plasminogen activator inhibitors which are immunologically similar to the plasminogen activator inhibitors from any of these sources also fall within the scope of the invention.

We claim:

1. A method of localizing an endothelial-type plasminogen activator inhibitor in a cell or tissue which comprises fixing the cell or tissue with a fixative, incubating the cell or tissue with a monoclonal antibody against human endothelial type plasminogen activator inhibitor, human ePAI, obtainable from dexamethasone-treated human HT-1080 fibrosarcoma cells, wherein said monoclonal antibody binds to an epitope of human ePAI that is not affected by said fixative and wherein said monoclonal antibody was raised against human ePAI obtained from dexamethasone-treated human HT1080 fibrosarcoma cells, and determining the regions of the cell or tissue to which said antibody has bound as an indication of the localization of endothelial-type plasminogen activator inhibitor present in the cell or tissue.

2. A method of detecting human ePAI in a sample which comprises incubating the sample with a monoclonal antibody, said monoclonal having been raised against human ePAI obtained from dexamethasone-treated human HT-1080 fibrosarcoma cells, and determining whether any human ePAI in the sample has been bound by said monoclonal antibody.

* * * * *